United States Patent
Kobayashi et al.

(10) Patent No.: US 12,343,030 B2
(45) Date of Patent: Jul. 1, 2025

(54) MOTIVE-POWER TRANSMITTING MECHANISM AND TREATMENT TOOL

(71) Applicant: OLYMPUS CORPORATION, Tokyo (JP)

(72) Inventors: Masayuki Kobayashi, Tokyo (JP); Noriaki Yamanaka, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 1199 days.

(21) Appl. No.: 17/154,032

(22) Filed: Jan. 21, 2021

(65) Prior Publication Data

US 2021/0137545 A1 May 13, 2021

Related U.S. Application Data

(63) Continuation of application No. PCT/JP2018/027608, filed on Jul. 24, 2018.

(51) Int. Cl.
*A61B 17/29* (2006.01)

(52) U.S. Cl.
CPC ...... *A61B 17/29* (2013.01); *A61B 2017/2905* (2013.01); *A61B 2017/2908* (2013.01);
(Continued)

(58) Field of Classification Search
CPC ............ A61B 17/29; A61B 2017/2905; A61B 2017/2908; A61B 2017/2927; A61B 2017/2937
(Continued)

(56) References Cited

U.S. PATENT DOCUMENTS

| 2005/0273084 A1 | 12/2005 | Hinman et al. |
| 2005/0273085 A1 | 12/2005 | Hinman et al. |

(Continued)

FOREIGN PATENT DOCUMENTS

| EP | 2113210 A2 | 11/2009 |
| EP | 3168013 A1 | 5/2017 |

(Continued)

OTHER PUBLICATIONS

International Search Report dated Oct. 16, 2018 issued in PCT/JP2018/027608.

*Primary Examiner* — Aaron F Roane
(74) *Attorney, Agent, or Firm* — Scully, Scott, Murphy & Presser, P.C.

(57) ABSTRACT

A motive-power transmitting mechanism includes: an elongated driving member that passes through a joint portion that can be flexed or bent and connects an end effector and a motive-power generating portion, and that transmits a motive power generated by the motive-power generating portion to the end effector; and a biasing member that expands/contracts between the driving member and a stationary member disposed in an area surrounding the driving member to bias the driving member, wherein the driving member generates a component force in a direction parallel to a longitudinal axis of the driving member on a basis of a biasing force of the biasing member, and the component force increases in a same direction as a direction of the motive power with an increase in a displacement amount of the driving member in a direction along the longitudinal axis in association with flexing or bending of the joint portion.

20 Claims, 15 Drawing Sheets

(52) U.S. Cl.
CPC ............ *A61B 2017/2927* (2013.01); *A61B 2017/2937* (2013.01)

(58) Field of Classification Search
USPC ............................................. 606/1
See application file for complete search history.

(56) References Cited

U.S. PATENT DOCUMENTS

| | | |
|---|---|---|
| 2009/0270853 A1 | 10/2009 | Yachi et al. |
| 2010/0234831 A1 | 9/2010 | Hinman et al. |
| 2010/0249759 A1 | 9/2010 | Hinman et al. |
| 2013/0060239 A1 | 3/2013 | Hinman et al. |
| 2013/0218141 A1 | 8/2013 | Hinman et al. |
| 2014/0367447 A1* | 12/2014 | Woodard, Jr. ... A61B 17/00234 227/176.1 |
| 2015/0119903 A1 | 4/2015 | Hinman et al. |
| 2015/0297865 A1 | 10/2015 | Hinman et al. |
| 2017/0105805 A1 | 4/2017 | Hasegawa et al. |
| 2018/0104448 A1 | 4/2018 | Hinman |
| 2020/0039093 A1 | 2/2020 | Yamanaka |
| 2020/0298419 A1 | 9/2020 | Kobayashi et al. |
| 2020/0324083 A1 | 10/2020 | Hinman et al. |

FOREIGN PATENT DOCUMENTS

| | | |
|---|---|---|
| JP | 2004-129871 A | 4/2004 |
| JP | 2009-261911 A | 11/2009 |
| JP | 2013-220107 A | 10/2013 |
| JP | 2013-240612 A | 12/2013 |
| JP | 2016-016242 A | 2/2016 |
| WO | WO 2005/120326 A2 | 12/2005 |
| WO | WO 2005/120327 A2 | 12/2005 |
| WO | WO 2018/193500 A1 | 10/2018 |
| WO | WO 2018/220844 A1 | 12/2018 |
| WO | WO 2019/116415 A1 | 6/2019 |

* cited by examiner

MOTIVE-POWER TRANSMITTING
MECHANISM AND TREATMENT TOOL

CROSS-REFERENCE TO RELATED
APPLICATIONS

This is a continuation of International Application PCT/JP2018/027608, with an international filing date of Jul. 24, 2018, which is hereby incorporated by reference herein in its entirety.

TECHNICAL FIELD

The present invention relates to a motive-power transmitting mechanism and a treatment tool.

BACKGROUND ART

In the related art, there is a known treatment tool: that includes an end effector provided at a distal end and an operating portion provided at a proximal end; and that causes the end effector to perform operations such as opening/closing by transmitting, to the end effector, a motive power imparted to the operating portion by an operator (for example, see Patent Literatures 1 and 2). As a motive-power transmitting member that transmits the motive power to the end effector from the operating portion, a cable is used in Patent Literature 1 and a slider portion is used in Patent Literature 2.

CITATION LIST

Patent Literature

{PTL 1} Japanese Unexamined Patent Application, Publication No. 2013-240612
{PTL 2} Japanese Unexamined Patent Application, Publication No. 2009-261911

SUMMARY OF INVENTION

An aspect of the present invention is directed to a motive-power transmitting mechanism including an elongated driving member that passes through a joint portion that can be flexed or bent and connects an end effector and a motive-power generating portion, and that transmits a motive power generated by the motive-power generating portion to the end effector; and a biasing member that expands/contracts between the driving member and a stationary member disposed in an area surrounding the driving member to bias the driving member, wherein the driving member generates a component force in a direction parallel to a longitudinal axis of the driving member on a basis of a biasing force of the biasing member, and the component force increases in a same direction as a direction of the motive power with an increase in a displacement amount of the driving member in a direction along the longitudinal axis in association with flexing or bending of the joint portion.

Another aspect of the present invention is directed to a treatment tool including: an end effector; a joint portion that can be flexed or bent; a motive-power generating portion that generates a motive power; an elongated driving member that passes through the joint portion and connects the end effector and the motive-power generating portion, and that transmits the motive power to the end effector; and a biasing member that expands/contracts between the driving member and a stationary member disposed in an area surrounding the driving member to bias the driving member, wherein the driving member generates a component force in a direction parallel to a longitudinal axis of the driving member on a basis of a biasing force of the biasing member, and the component force increases in a same direction as a direction of the motive power with an increase in a displacement amount of the driving member in a direction along the longitudinal axis in association with flexing or bending of the joint portion.

DESCRIPTION OF EMBODIMENT

A motive-power transmitting mechanism 1 and a treatment tool 2 according to an embodiment of the present invention will be described below with reference to the drawings.

Figure 1:
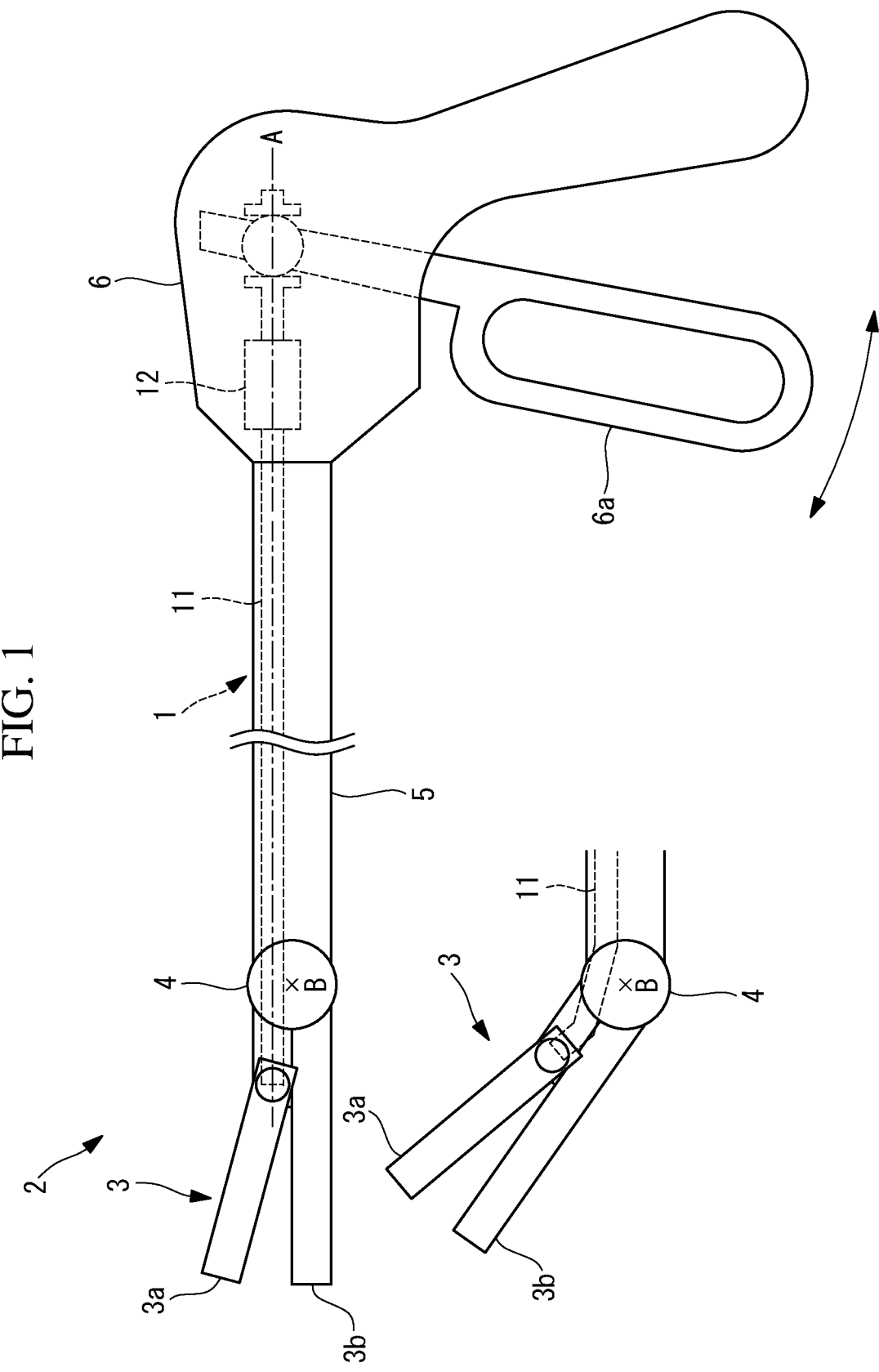
FIG. 1 is an overall configurational diagram of a treatment tool according to an embodiment of the present invention.

As shown in FIG. 1, the treatment tool 2 according to this embodiment includes: an end effector 3, a joint portion 4, an elongated insertion portion 5 extending along a longitudinal axis A, and an operating portion (motive-power generating portion) 6, which are disposed along the longitudinal axis A in this order from a distal-end side. In addition, the treatment tool 2 includes the motive-power transmitting mechanism 1 that transmits a motive power to the end effector 3 from the operating portion 6.

The joint portion 4 can be flexed about a flexion axis B that is orthogonal to the longitudinal axis A. The end effector 3 is gripping forceps having a pair of gripping pieces 3a and 3b, which can be opened/closed with respect to each other, and can be pivoted about the flexion axis B by means of flexing of the joint portion 4. The end effector 3 is closed by means of a pushing force that is transmitted thereto from the motive-power transmitting mechanism 1 and that is directed toward a distal end and is opened by means of a pulling force that is transmitted thereto from the motive-power transmitting mechanism 1 and that is directed toward a proximal end. Therefore, the magnitude of a gripping force Fg generated in the end effector 3 is controlled by a pushing force Fout from the motive-power transmitting mechanism 1 (see FIG. 2C).

Note that the end effector 3 is not limited to gripping forceps, and another type of end effector (for example, a knife) that performs a mechanical operation in accordance with a motive power may be employed. Alternatively, the end effector 3 may be configured so that a joint portion provided in the end effector 3 is driven by the motive power from the motive-power transmitting mechanism 1.

The operating portion 6 is connected to a proximal end of the insertion portion 5. The operating portion 6 includes a handle 6a that is manually operated by an operator to perform opening/closing operations of the end effector 3. The operating portion 6 generates a pushing force when the handle 6a is operated in the closing direction and generates a pulling force when the handle 6a is operated in the opening direction. The pushing force and the pulling force are transmitted to a proximal-end portion of a driving member 11 (described later) of the motive-power transmitting mechanism 1. The handle 6a is a handle of an arbitrary form such as a lever system or a rotating system. The operating portion 6 includes another handle (not shown) that is manually operated by the operator to perform a flexing operation of the joint portion 4.

As shown in FIG. 1, the motive-power transmitting mechanism 1 includes the driving member 11 that transmits a motive power to the end effector 3 from the operating portion 6 and an adjusting mechanism 12 that adjusts the magnitude of the motive power transmitted by the driving member 11.

The driving member 11 is an elongated member disposed inside the insertion portion 5 along the longitudinal axis A. The driving member 11 passes through the joint portion 4 and extends to the operating portion 6 from the end effector 3. A distal-end portion of the driving member 11 is connected to the end effector 3 and a proximal-end portion of the driving member 11 is connected to the handle 6a of the operating portion 6. The driving member 11 can be moved along the longitudinal axis A in accordance with the pushing force and the pulling force applied thereto from the operating portion 6. The driving member 11 can be flexed or bent at the joint portion 4 while being capable of transmitting the motive power along the longitudinal direction at a high efficiency. For example, the driving member 11 is formed of a plurality of linkages that are linked with each other in a pivotable manner or a wire possessing flexibility.

Figure 2A:
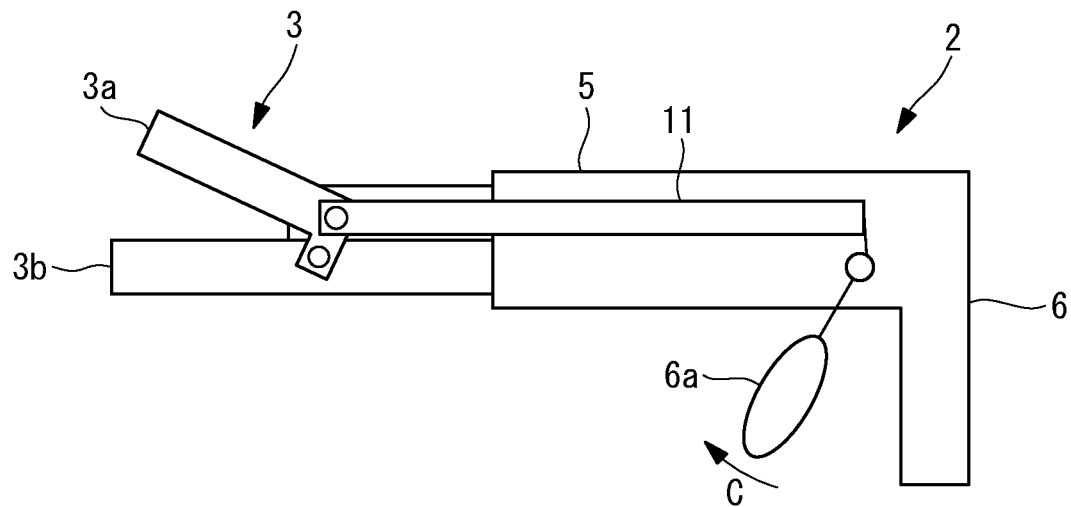
FIG. 2A is a schematic diagram of the treatment tool showing an open state of an end effector.
Figure 2B:
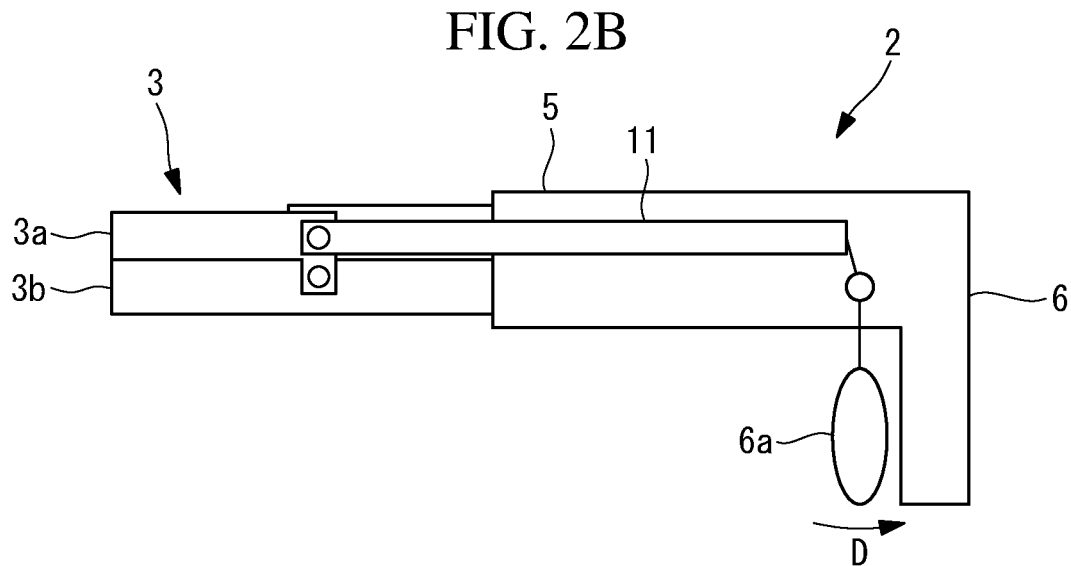
FIG. 2B is a schematic diagram of the treatment tool showing a closed state of the end effector.
Figure 2C:
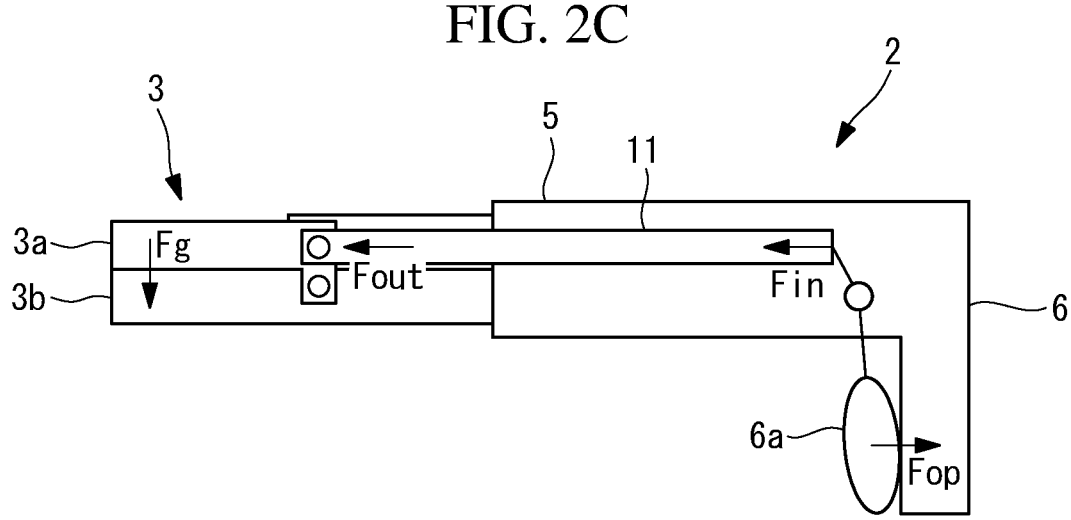
FIG. 2C is a schematic diagram of the treatment tool showing a gripped state of the end effector.

FIG. 2A shows an open state of the end effector 3, FIG. 2B shows a closed state of the end effector 3, and FIG. 2C shows a gripping operation of the end effector 3. In FIGS. 2A to 2C, some parts of the configuration are omitted from the illustration in order to simplify the illustration.

As shown in FIG. 2A, the driving member 11 is pulled as a result of the handle 6a being operated in an opening direction C, which in turn causes the driving member 11 to be retracted toward the proximal end, and thus, the end effector 3 is opened. As shown in FIG. 2B, the driving member 11 is pushed as a result of the handle 6a being operated in a closing direction D, which in turn causes the driving member 11 to be advanced toward the distal end, and thus, the end effector 3 is closed. In the closed state in FIG. 2B, the pair of gripping pieces 3a and 3b are lightly in contact with each other. Accordingly, opening/closing of the end effector 3 is performed via the movements of the driving member 11. Therefore, almost no force is required to operate the handle 6a to perform the opening/closing operations of the end effector 3.

On the other hand, in the gripping operation of the end effector 3, an operating force Fop in the closing direction D is applied to the handle 6a when the end effector 3 is in the closed state. Accordingly, as shown in FIG. 2C, a pushing force (motive power) Fin of a magnitude in accordance with the operating force Fop is input to the proximal-end portion of the driving member 11, and the gripping force Fg of a magnitude in accordance with the pushing force Fin is generated between the pair of gripping pieces 3a and 3b.

Next, the operation of the driving member 11 and the motive-power transmission efficiency thereof when the joint portion 4 is flexed about the flexion axis B will be described.

Figure 3:
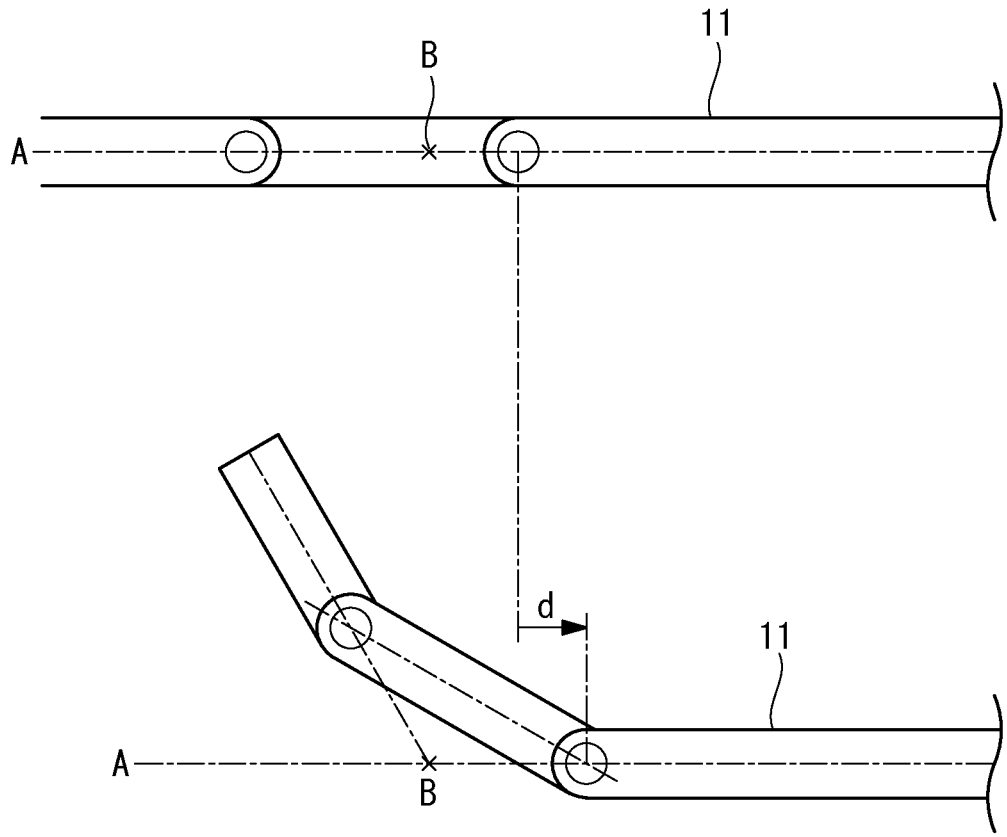
FIG. 3 is a diagram for explaining displacement of a driving member due to flexing of a joint portion and shows a state in which the joint portion is not flexed (top) and a state in which the joint portion is flexed (bottom).

In FIG. 3, a state in which the joint portion 4 is not flexed (a state in which the end effector 3 and the insertion portion 5 are disposed in a single row on a straight line) is shown at the top and a state in which the joint portion 4 is flexed is shown at the bottom. The position of the proximal end of the driving member 11 in the state in which the joint portion 4 is not flexed is defined as the reference position.

Figure 4:
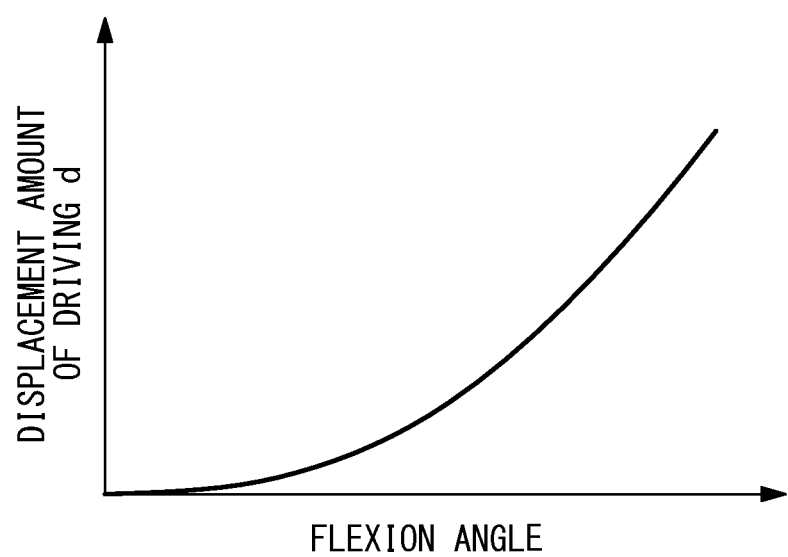
FIG. 4 is a graph showing the relationship between the flexion angle of the joint portion and the displacement amount of the driving member.

When the joint portion 4 is flexed about the flexion axis B, the proximal end of the driving member 11 is displaced toward the proximal end from the reference position. This is a result of a pathway length of the driving member 11 in the joint portion 4 being reduced as a result of the driving member 11 that is flexed or bent in the joint portion 4 being displaced radially inward, as shown in FIG. 3. A displacement amount d of the driving member 11 increases with an increase in the flexion angle of the joint portion 4, as shown in FIG. 4.

Figure 5:
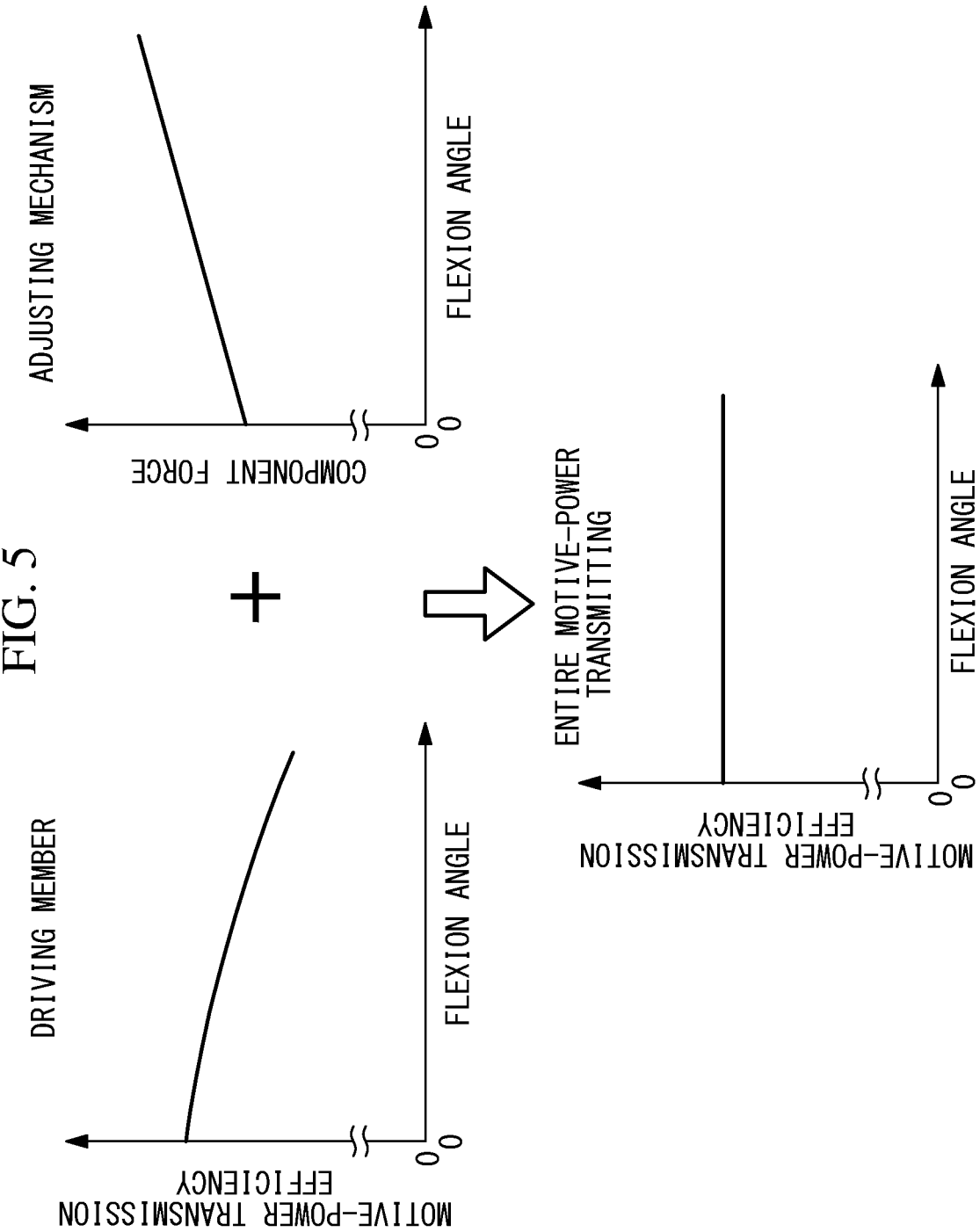
FIG. 5 is a graph showing the relationship between the flexion angle of the joint portion and the motive-power transmission efficiency of the driving member, as well as that of the entire motive-power transmitting mechanism.

In contrast, regarding the motive-power transmission efficiency, the motive-power transmission efficiency of the driving member 11 deteriorates with an increase in the flexion angle of the joint portion 4, as shown in FIG. 5. This is a result of a loss occurring in the motive power transmitted via the driving member 11 as a result of an increase in the friction between the flexed (or bent) driving member 11 and peripheral members. An additional cause is that a loss occurs in a component of the motive power in a direction orthogonal to the longitudinal axis A in accordance with the angles between the linkages as a result of flexing of the linkages constituting the driving member 11.

Figure 6:
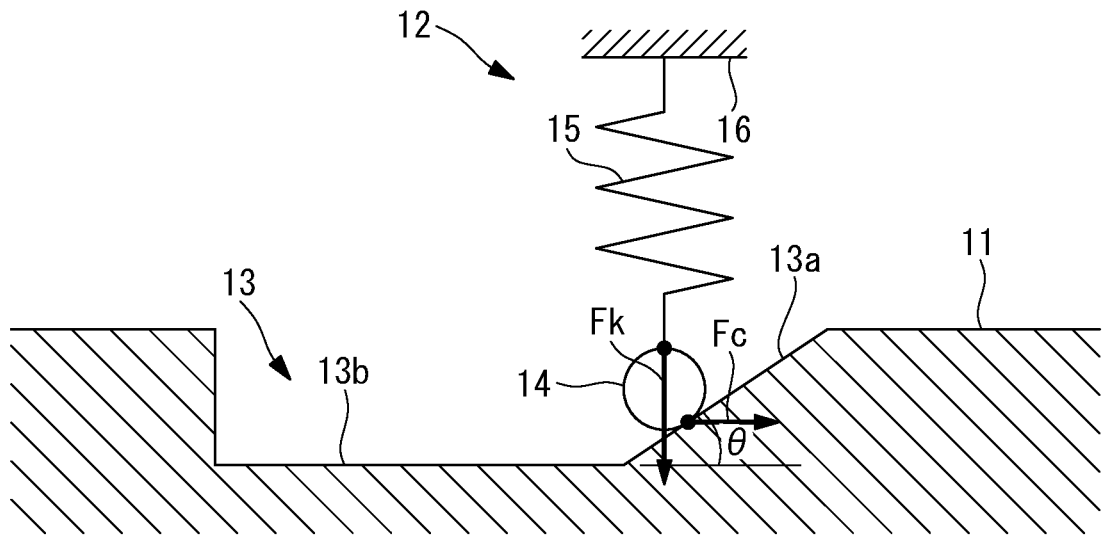
FIG. 6 is a configuration diagram of an adjusting mechanism included in the motive-power transmitting mechanism of the treatment tool in FIG. 1.
Figure 7:
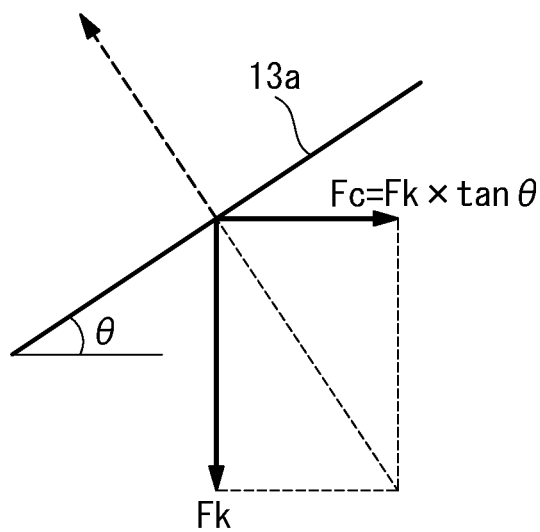
FIG. 7 is a diagram for explaining a component force generated at an inclined surface of the adjusting mechanism in FIG. 6.

As shown in FIG. 6, the adjusting mechanism 12 includes: a force receiving portion 13 that is provided in the driving member 11 and that has an inclined surface 13a; a movable member 14 that can be slid along the inclined surface 13a; and a compression spring (biasing member) 15 that biases the movable member 14 toward the inclined surface 13a. As shown in FIG. 7, the adjusting mechanism 12 generates, by means of the inclined surface 13a, a component force Fc from an elastic force Fk of the compression spring 15. As a result of the component force Fc being combined with the pushing force Fin, the pushing force Fout to be output to the end effector 3 from the driving member 11 is adjusted.

The force receiving portion 13 is a slit that is formed in a side surface of the driving member 11 and that extends in the longitudinal direction. The slit 13 has a depth in a width direction of the driving member 11 orthogonal to the longitudinal axis A. The movable member 14 is disposed in the slit 13 and moves in the slit 13 in a direction along the longitudinal axis A in association with the movement of the driving member 11 in the longitudinal direction in the opening/closing operations and the gripping operation of the end effector 3.

The inclined surface 13a is part of a bottom surface of the slit 13. The inclined surface 13a is inclined, toward the proximal end from the distal-end side, with respect to the longitudinal axis A in a direction in which a displacement gradually occurs outward in a width direction, and a proximal end of the inclined surface 13a is positioned farther outside in the width direction than a distal end of the inclined surface 13a is. An inclination angle $\theta$ of the inclined surface 13a with respect to the longitudinal axis A is constant.

The movable member 14 is, for example, a cylindrical pin.

The compression spring 15 is disposed between the movable member 14 and a stationary member 16, one end of the compression spring 15 is secured to the movable member 14, and the other end of the compression spring 15 is secured to the stationary member 16. The stationary member 16 is a member that is disposed in an area surrounding the driving member 11, and is secured with respect to the insertion portion 5 and the operating portion 6. The compression spring 15 can be expanded/contracted in the width direction of the driving member 11. Therefore, the movable member 14 is supported by the stationary member 16 so as to be movable in the width direction by means of the compression spring 15.

The compression spring 15 is compressed when the movable member 14 is positioned on the inclined surface 13a and generates the elastic force Fk in accordance with the compression amount. The movable member 14 is biased toward the inclined surface 13a by means of the elastic force Fk of the compression spring 15, and the elastic force Fk in the width direction acts on the inclined surface 13a from the movable member 14. Because the inclined surface 13a is inclined with respect to the direction of the elastic force Fk, the component force Fc=Fk×tan $\theta$ in the direction along the longitudinal axis A is generated, as shown in FIG. 7. The direction of the component force Fc is opposite from the direction of the pushing force Fin.

Figure 8A:
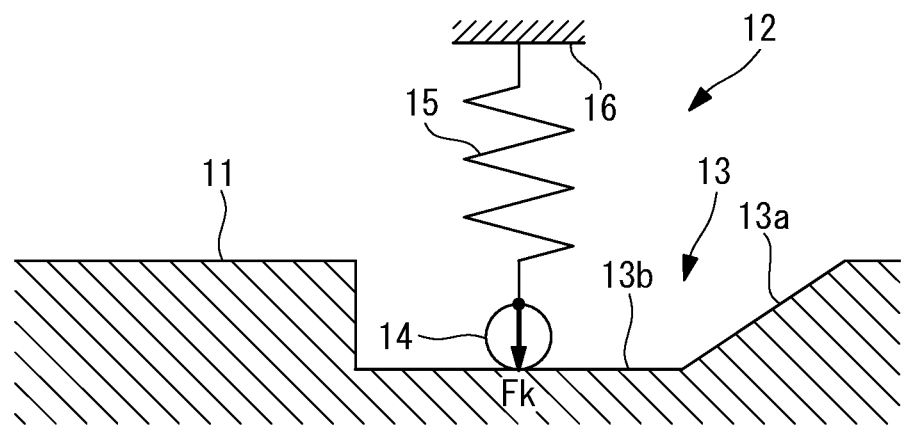
FIG. 8A is a diagram for explaining the operation of the adjusting mechanism in FIG. 6 and shows the positional relationship between the inclined surface and a movable member when the end effector is in the open state.
Figure 8B:
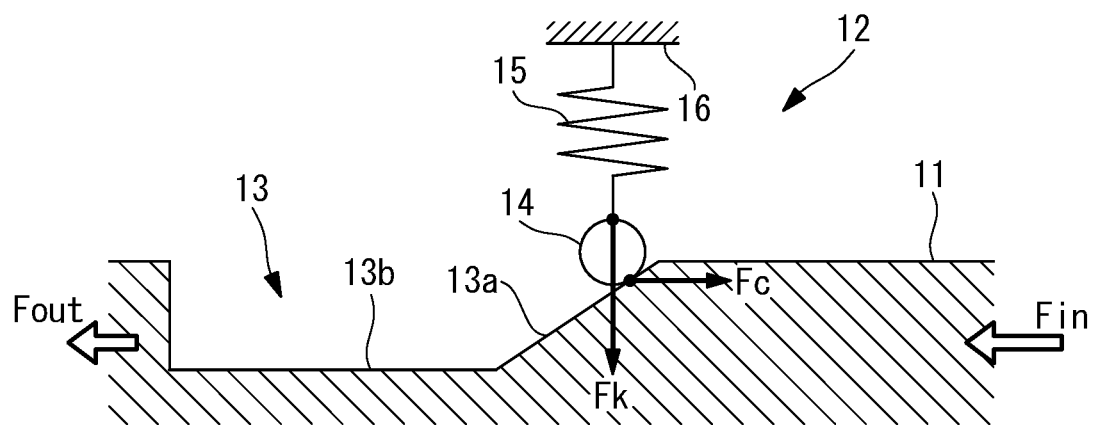
FIG. 8B is a diagram for explaining the operation of the adjusting mechanism in FIG. 6 and shows the positional relationship between the inclined surface and the movable member when the end effector is in the gripped state and the joint portion is not flexed.
Figure 8C:
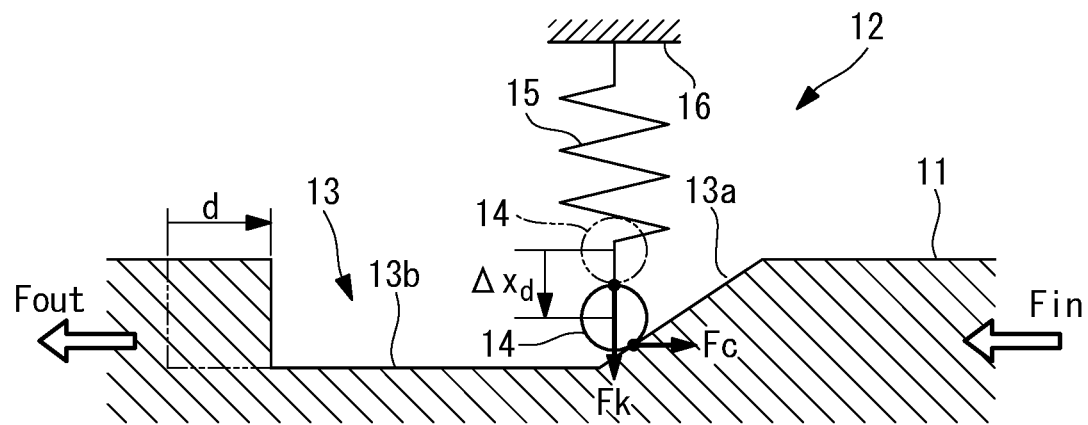
FIG. 8C is a diagram for explaining the operation of the adjusting mechanism in FIG. 6 and shows the positional relationship between the inclined surface and the movable member when the end effector is in the gripped state and the joint portion is flexed.

FIG. 8A shows the positional relationship between the driving member 11 and the movable member 14 when the end effector 3 is in the open state. FIGS. 8B and 8C show the positional relationship between the driving member 11 and the movable member 14 when the end effector 3 is disposed in the gripped state. FIG. 8B shows the state in which the joint portion 4 is not flexed, and FIG. 8C shows the state in which the joint portion 4 is flexed.

In the process in which the end effector 3 closes so as to enter the closed state from the open state, as a result of the driving member 11 moving toward the distal end, the movable member 14 is displaced in a direction in which the movable member 14 is brought close to the stationary member 16 along the inclined surface 13a, and the compression spring 15 is compressed. Therefore, when the end effector 3 is in the gripped state, the movable member 14 is positioned on the inclined surface 13a, and the component force Fc based on the elastic force Fk of the compression spring 15 acts on the driving member 11.

As shown in FIG. 8B, when the joint portion 4 is not flexed, the compression amount of the compression spring 15 is $\Delta x_0$, the elastic force Fk is $k \times \Delta x_0$, and the component force Fc is $k \times \Delta x_0 \times \tan \theta$. Therefore, the pushing force Fout (=Fin−Fc) after the adjustment by the adjusting mechanism 12 is Fin−k×$\Delta x_0$×tan $\theta$. k is the spring constant of the compression spring 15. In contrast, as shown in FIG. 8C when the joint portion 4 is flexed, as a result of the driving member 11 being displaced toward the proximal end by an amount corresponding to the displacement amount d, the movable member 14 is displaced by an amount corresponding to $\Delta x_d = d \times \tan \theta$ in a direction away from the stationary member 16, the elastic force Fk decreases by an amount corresponding to $k \times \Delta x_d$, and the magnitude of the component force Fc decreases by an amount corresponding to $k \times \Delta x_d \times \tan \theta$. Therefore, the pushing force Fout is Fin−k× $(\Delta x_0 - \Delta x_d) \times \tan \theta$.

As has been described above, as a result of flexing of the joint portion 4, the magnitude of the component force Fc decreases, and Fout increases by the amount corresponding to $k \times \Delta x_d \times \tan \theta$. With an increase in the displacement amount d of the driving member 11, a displacement amount $\Delta x_d$ of the movable member 14 in the direction away from the stationary member 16 increases and the magnitude of the component force Fc decreases. In other words, as shown in FIG. 5, with increases in the flexion angle of the joint portion 4 and the displacement amount d, the component force Fc increases in the same direction as the direction of the pushing force Fin.

Next, the operation of the thus-configured motive-power transmitting mechanism 1 and treatment tool 2 will be described.

In order to treat an affected area by employing the treatment tool 2 according to this embodiment, the insertion portion 5 is inserted into a body, the end effector 3 at the distal end thereof is disposed in the vicinity of the affected area, and the orientation of the end effector 3 with respect to the affected area is adjusted by flexing the joint portion 4 by operating the handle of the operating portion 6 for performing the flexing operation.

Next, the end effector 3 is opened by operating the handle 6a in the opening direction, and the affected area is disposed between the pair of gripping pieces 3a and 3b. Next, as a result of closing the end effector 3 by operating the handle 6a in the closing direction, the affected area is sandwiched between the pair of gripping pieces 3a and 3b. Subsequently, as a result of applying the operating force Fop in the closing direction to the handle 6a, the gripping force Fg is generated between the pair of gripping pieces 3a and 3b. In other words, the pushing force Fin corresponding to the operating force Fop is transmitted to the end effector 3 from the operating portion 6 via the driving member 11. The pair of gripping pieces 3a and 3b firmly grip the affected area with the gripping force Fg, the magnitude of which corresponds to the operating force Fop.

In this case, in the state in which the joint portion 4 is flexed, the motive-power transmission efficiency of the driving member 11 deteriorates, as shown in FIG. 5. The amount by which the motive-power transmission efficiency of the driving member 11 deteriorates increases with an increase in the flexion angle of the joint portion 4.

Meanwhile, when the end effector 3 is in the gripped state, the component force Fc that is in the opposite direction from the direction of the pushing force Fin acts on the driving member 11 as a result of the elastic force Fk of the compression spring 15 acting on the inclined surface 13a from the movable member 14. The component force Fc increases in the same direction as the direction of the pushing force Fin with increases in the flexion angle of the joint portion 4 and the displacement amount d of the driving member 11.

Specifically, with this embodiment, an increase in the component force Fc compensates for the deterioration of the motive-power transmission efficiency of the driving member 11 associated with flexing of the joint portion 4. Therefore, it is possible to keep the motive-power transmission efficiency of the entire motive-power transmitting mechanism 1 substantially constant regardless of the flexion angle of the joint portion 4. Specifically, the relationship between the operating force Fop applied to the handle 6a and the gripping force Fg of the end effector 3 is kept substantially constant regardless of the flexion angle of the joint portion 4. Accordingly, there is an advantage in that the operator can accurately control the gripping force Fg by means of the operating force Fop applied to the handle 6a.

In addition, the adjusting mechanism 12 is configured in a simple manner by combining the inclined surface 13a, the movable member 14, and the compression spring 15. With such an adjusting mechanism 12, there is an advantage in that it is possible to cause the component force Fc to act on the driving member 11 without influencing the design and operation of the driving member 11 and the handle 6a with which the driving member 11 is operated. In addition, there is an advantage in that the design and assembly of the adjusting mechanism 12 for generating a desired component force Fc are facilitated.

It is preferable that a portion 13b of a bottom surface of the slit 13 on which the movable member 14 slides during the opening/closing operations of the end effector 3 be substantially parallel to the longitudinal direction of the driving member 11, and it is preferable that the length or the like of the compression spring 15 be designed so that the compression amount of the compression spring 15 becomes zero during the opening/closing operations of the end effector 3. Accordingly, it is possible to prevent the elastic force Fk from acting on the driving member 11 from the movable member 14 during the opening/closing operations of the end effector 3.

Figure 9:
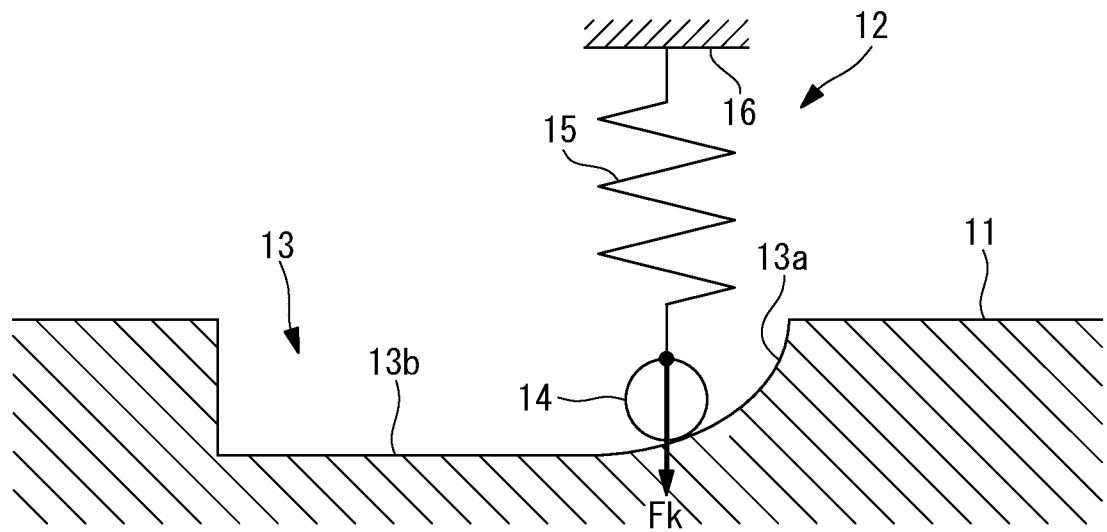
FIG. 9 is a diagram showing a modification of the inclined surface in the adjusting mechanism in FIG. 6.
Figure 10:
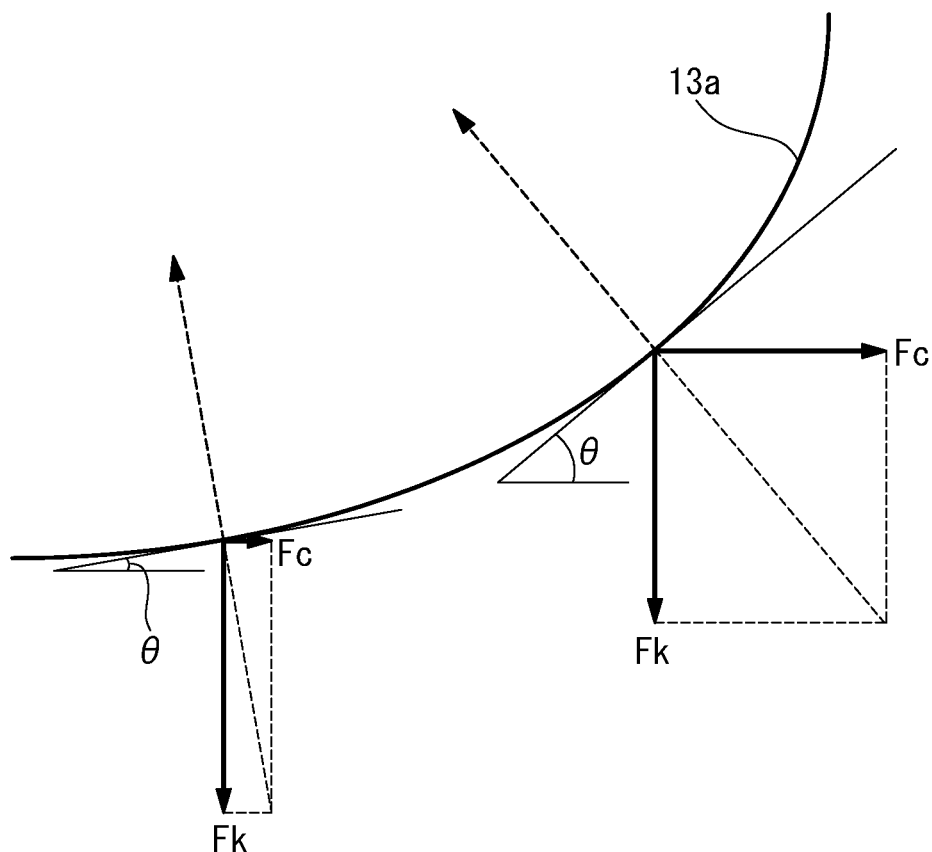
FIG. 10 is a diagram for explaining a component force that the inclined surface in FIG. 9 generates.

In this embodiment, the inclined surface 13a is a flat surface having a constant inclination angle $\theta$; however, alternatively, the inclined surface 13a may be a curved surface, and the inclination angle $\theta$ may continuously and monotonically change in the direction along the longitudinal axis A, as shown in FIG. 9. In this case, as shown in FIG. 10, the component force Fc changes in accordance with changes in both of the elastic force Fk and the inclination angle $\theta$. Therefore, the magnitude of the component force Fc nonlinearly changes in accordance with the displacement amount d of the driving member 11, and the rate of change of the pushing force Fout changes.

In order to decrease the magnitude of the component force Fc depending on the displacement amount d, the elastic force Fk of the compression spring 15 and the inclination angle $\theta$ satisfy Expression (1) below:

$$Fk1 \times \tan \theta 1 > Fk2 \times \tan \theta 2 \tag{1},$$

where Fk1 is the magnitude of the elastic force that the compression spring 15 generates when the end effector 3 is in the gripped state and the joint portion 4 is not flexed. $\theta 1$ is the inclination angle of the inclined surface 13a at a contact point with the movable member 14 when the end effector 3 is in the gripped state and the joint portion 4 is not flexed. Fk2 is the magnitude of the elastic force that the compression spring 15 generates when the end effector 3 is in the gripped state and the joint portion 4 is flexed. $\theta 2$ is the inclination angle of the inclined surface 13a at the contact point with the movable member 14 when the end effector 3 is in the gripped state and the joint portion 4 is flexed.

Furthermore, the inclination angle $\theta$ and the compression amount of the compression spring 15 are designed so that the rate of change of the component force Fc becomes a desired rate of change.

As shown in FIG. 5, the deterioration rate of the motive-power transmission efficiency of the driving member 11 increases with an increase in the flexion angle of the joint portion 4. Therefore, it is preferable that the inclination angle θ be designed so that the rate of change of the component force Fc increases with an increase in the displacement amount d of the driving member 11. In the case of the example in FIGS. 9 and 10, the inclination angle θ gradually decreases toward the distal end from the proximal-end side. For example, it is preferable that the shape of the inclined surface 13a be a logarithmically curved shape.

In this embodiment, the elastic force of the compression spring 15 is employed as the biasing force for biasing the movable member 14; however, alternatively, forces generated by other members may be employed.

Figure 11:
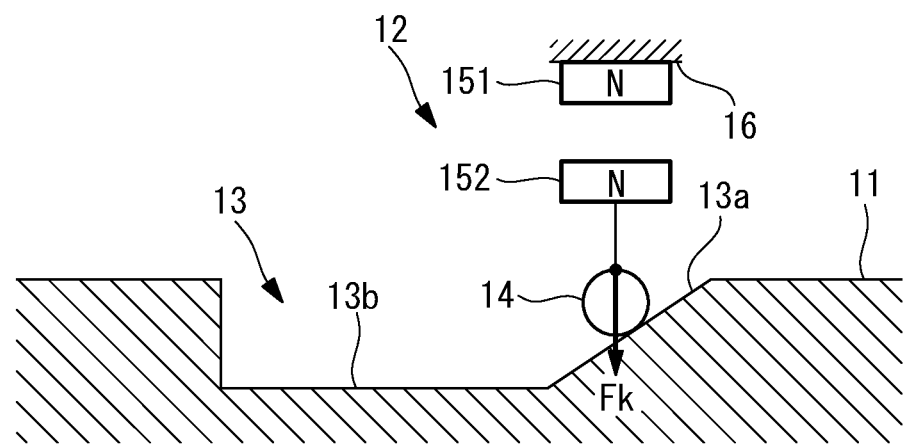
FIG. 11 is a diagram showing a modification of a biasing member of the adjusting mechanism in FIG. 6.
Figure 12:
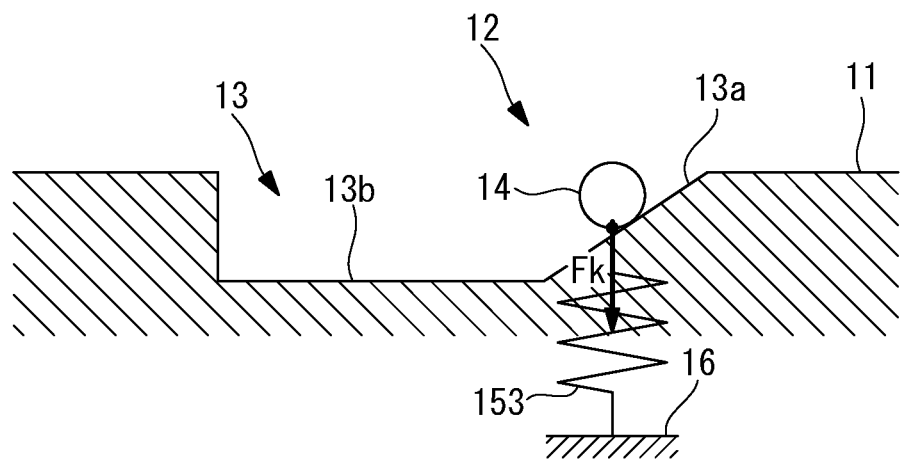
FIG. 12 is a diagram showing another modification of the biasing member of the adjusting mechanism in FIG. 6.
Figure 13:
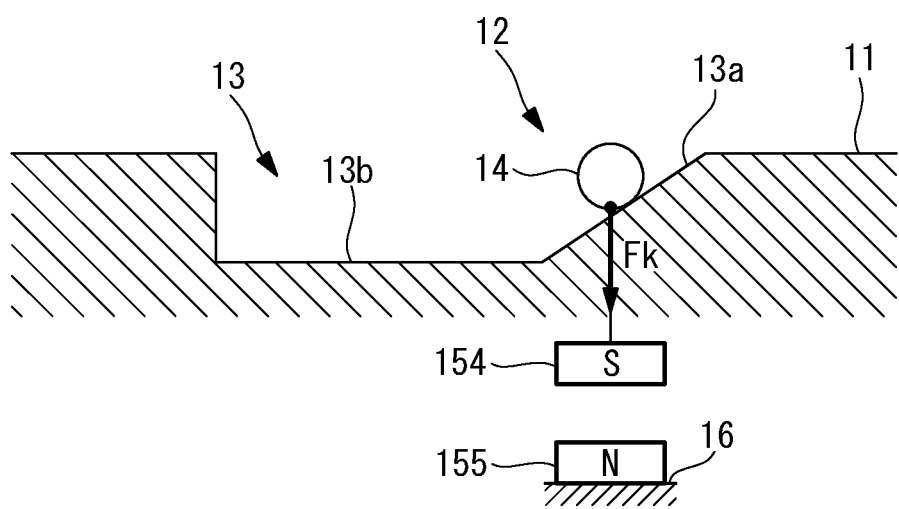
FIG. 13 is a diagram showing another modification of the biasing member of the adjusting mechanism in FIG. 6.

FIGS. 11 to 13 show modifications of the biasing member.

In FIG. 11, the biasing member is a pair of magnets 151 and 152 that are disposed on the same side as the movable member 14 with respect to the inclined surface 13a and that generate repulsive forces with respect to each other. The magnet 151 is secured to the stationary member 16 and the magnet 152 is secured to the movable member 14. The repulsive forces between the pair of magnets 151 and 152 are biasing forces Fk. The distance between the magnets 151 and 152 changes in accordance with the displacement amount d, and the magnitude of the repulsive forces Fk changes.

In FIG. 12, the biasing member is a tension spring 153 that is disposed on the opposite side from the movable member 14 with respect to the inclined surface 13a. The elastic force of the tension spring 153 is the biasing force Fk. The tension amount of the tension spring 153 changes in accordance with the displacement amount d, and the magnitude of the elastic force Fk changes.

In FIG. 13, the biasing member is a pair of magnets 154 and 155 that are disposed on the opposite side from the movable member 14 with respect to the inclined surface 13a and that generate attractive forces with respect to each other. The magnet 155 is secured to the stationary member 16 and the magnet 154 is secured to the movable member 14. The attractive forces between the pair of magnets 154 and 155 are biasing forces Fk. The distance between the magnets 154 and 155 changes in accordance with the displacement amount d, and the magnitude of the attractive forces Fk changes.

Figure 14:
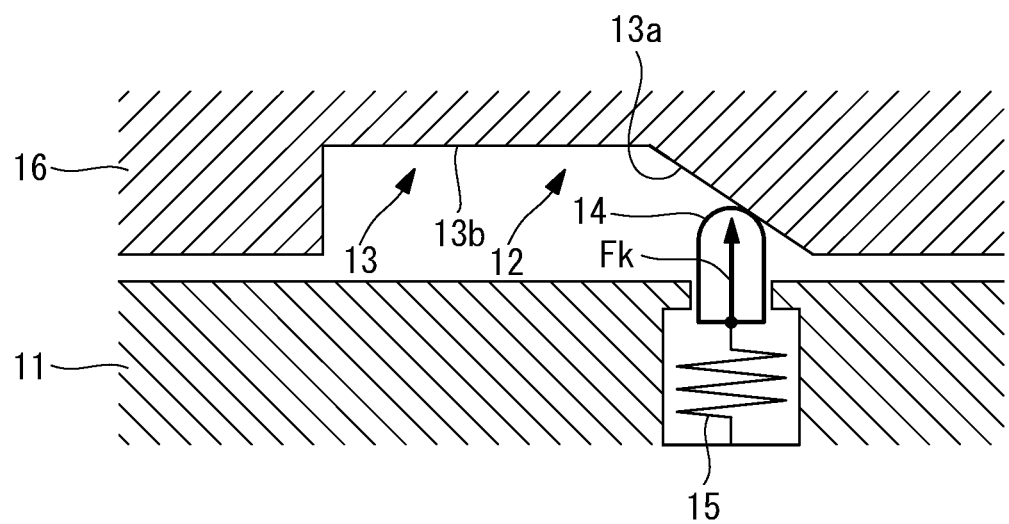
FIG. 14 is a diagram showing a modification of a manner in which the inclined surface, the movable member, and the biasing member of the adjusting mechanism in FIG. 6 are disposed.

In this embodiment, the force receiving portion 13 having the inclined surface 13a is provided in the driving member 11 and the movable member 14 is supported with respect to the stationary member 16 by means of the compression spring 15; however, alternatively, the movable member 14 may be supported with respect to the driving member 11 by means of the compression spring 15 and the force receiving portion 13 may be formed in the stationary member 16, as shown in FIG. 14.

As has been described above, even if the arrangements of the force receiving portion 13 and the movable member 14 are reversed, it is possible to increase the component force Fc in the same direction as the direction of the pushing force Fin with an increase in the displacement amount d by causing the component force Fc to act on the driving member 11.

Figure 15:
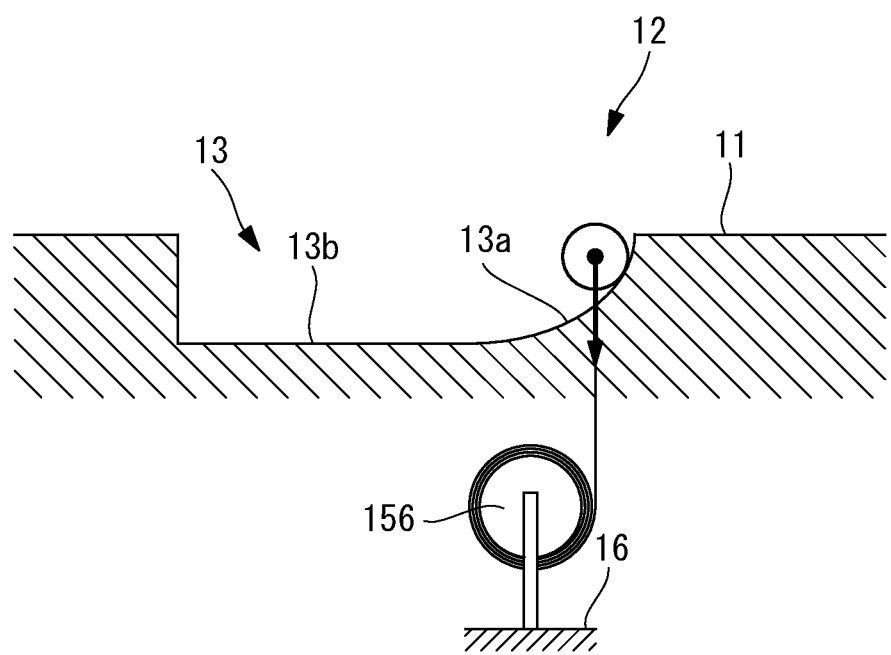
FIG. 15 is a diagram showing another modification of the biasing member of the adjusting mechanism in FIG. 6.

In this embodiment, the biasing force Fk generated by the biasing member 15 changes in accordance with the displacement amount d; however, alternatively, the biasing force Fk may be constant regardless of the displacement amount d. For example, as shown in FIG. 15, a constant-load spring 156 may be employed as the biasing member. In this case, in order to change the component force Fc in accordance with the displacement amount d, the inclined surface 13a is a curved surface in which the inclination angle θ monotonically changes.

In this embodiment, the adjusting mechanism 12 generates the component force Fc in the opposite direction from the direction of the pushing force Fin; however, alternatively, the adjusting mechanism 12 may generate a component force Fc in the same direction as the direction of the pushing force Fin. For example, as shown in FIGS. 16A and 16B, the inclined surface 13a may be inclined, toward the proximal end from the distal-end side, with respect to the longitudinal axis A in a direction in which a displacement gradually occurs inward in a width direction.

Figure 16A:
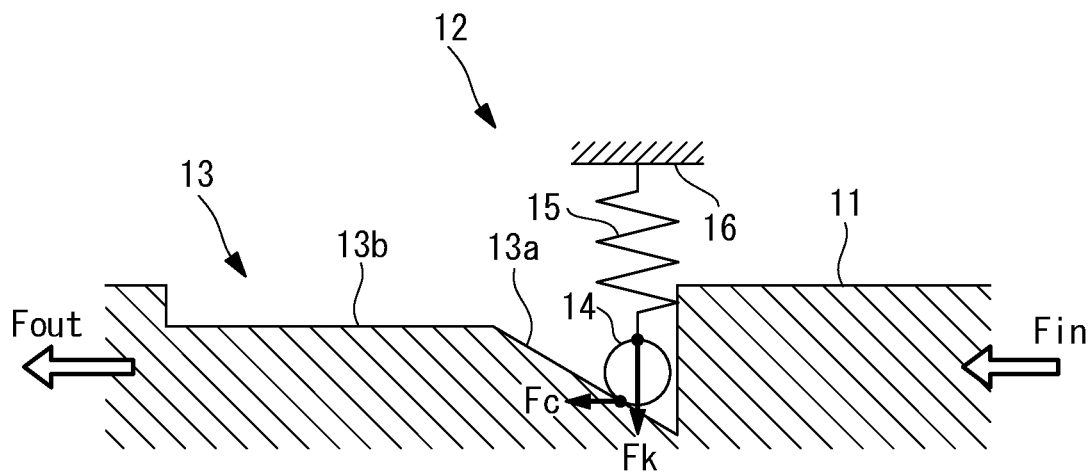
FIG. 16A is a diagram showing a modification of the adjusting mechanism in FIG. 6 and shows the positional relationship between the inclined surface and the movable member when the end effector is in the gripped state and the joint portion is not flexed.

When the end effector 3 is in the gripped state and the joint portion 4 is not flexed, as shown in FIG. 16A, the pushing force Fout becomes $Fin + k \times \Delta x_0 \times \tan \theta$. On the other hand, when the end effector 3 is in the gripped state and the joint portion 4 is flexed, as shown in FIG. 16B, as the result of the driving member 11 being displaced by the amount corresponding to the displacement amount d, the compression amount of the compression spring 15 increases by the amount corresponding to $\Delta x_d$. Therefore, the pushing force Fout is $Fin + k \times (\Delta x_0 + \Delta x_d) \times \tan \theta$. In this way, with the modification in FIGS. 16A and 16B, the pushing force Fout increases as compared with the case in which the direction of the component force Fc is opposite from the direction of the pushing force Fin. Therefore, it is possible to obtain a greater gripping force Fg.

Figure 16B:
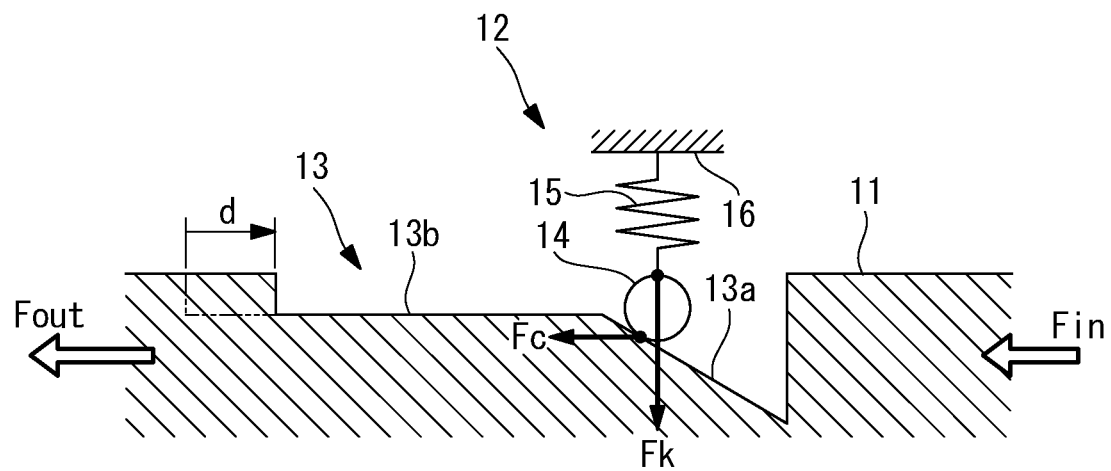
FIG. 16B is a diagram showing a modification of the adjusting mechanism in FIG. 6 and shows the positional relationship between the inclined surface and the movable member when the end effector is in the gripped state and the joint portion is flexed.

As in FIGS. 16A and 16B, in the case in which the direction of the component force Fc is the same as the direction of the pushing force Fin, the component force Fc prevents the retracting operation of the driving member 11 after the component force Fc increases as a result of the operating force Fop being applied to the handle 6a. Therefore, the operation of the handle 6a for shifting the end effector 3 to the closed state or the open state from the gripped state requires a large force. In order to eliminate such a problem, it is preferable that a releasing mechanism that releases biasing of the movable member 14 by the compression spring 15 be provided.

Figure 17:
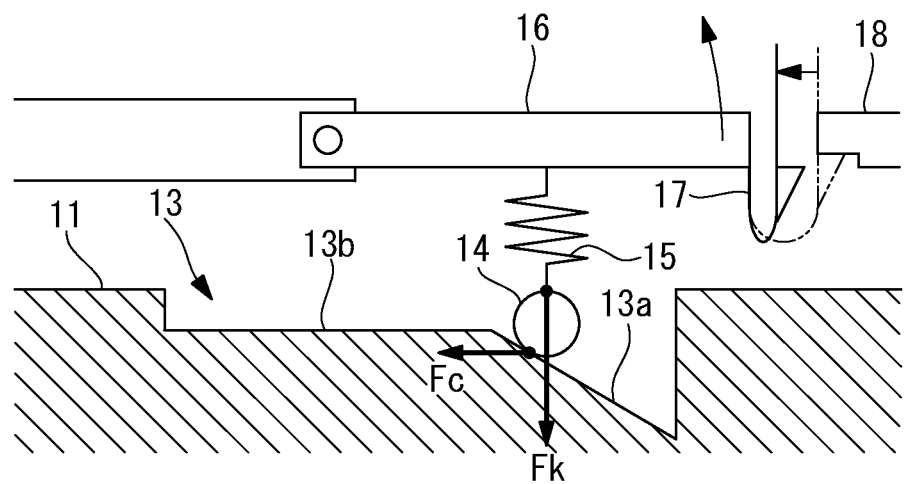
FIG. 17 is a diagram showing a configuration example of a releasing mechanism.

FIG. 17 shows an example of the releasing mechanism. In the releasing mechanism in FIG. 17, the stationary member 16 is pivotable and is linked to another member 18 in the area surrounding the stationary member 16 by means of a plate spring 17. As a result of the plate spring 17 being pushed, the linkage with the other member 18 by means of the plate spring 17 is released, the stationary member 16 is pivoted by the elastic force of the compression spring 15, and the compression spring 15 returns to the natural state.

Figure 18A:
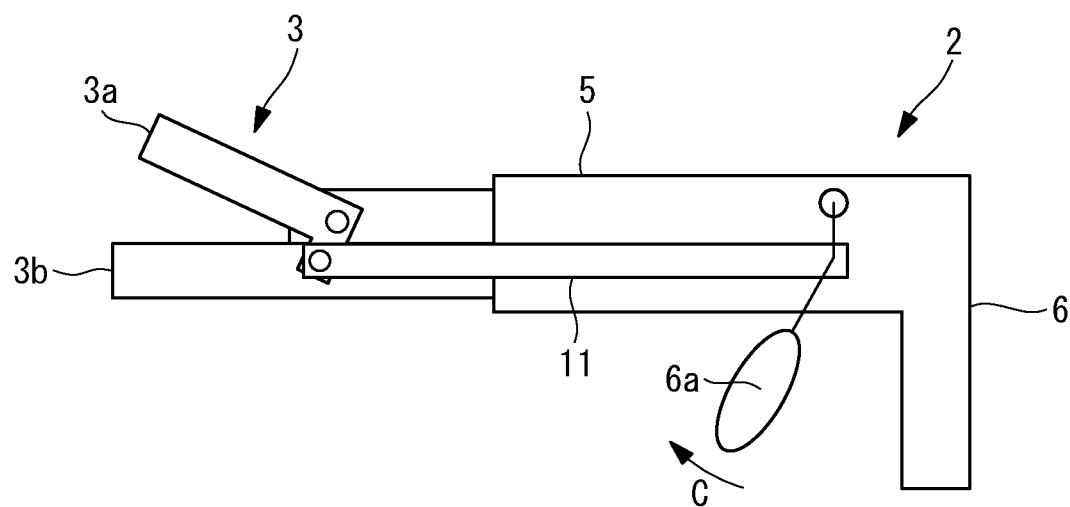
FIG. 18A is a schematic diagram of a modification of the treatment tool in FIG. 1 and shows the open state of the end effector.
Figure 18B:
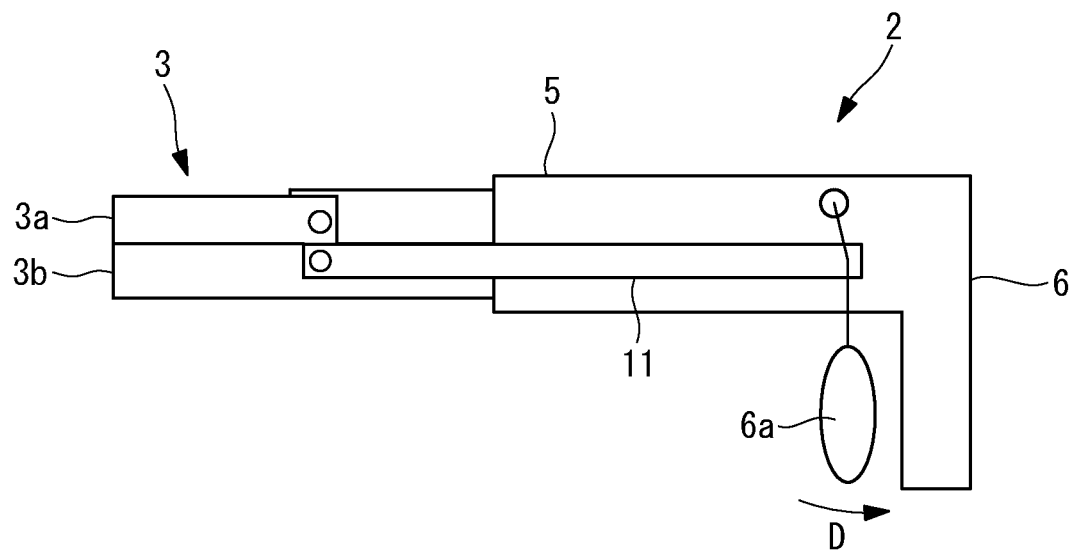
FIG. 18B is a schematic diagram of a modification of the treatment tool in FIG. 1 and shows the closed state of the end effector.
Figure 18C:
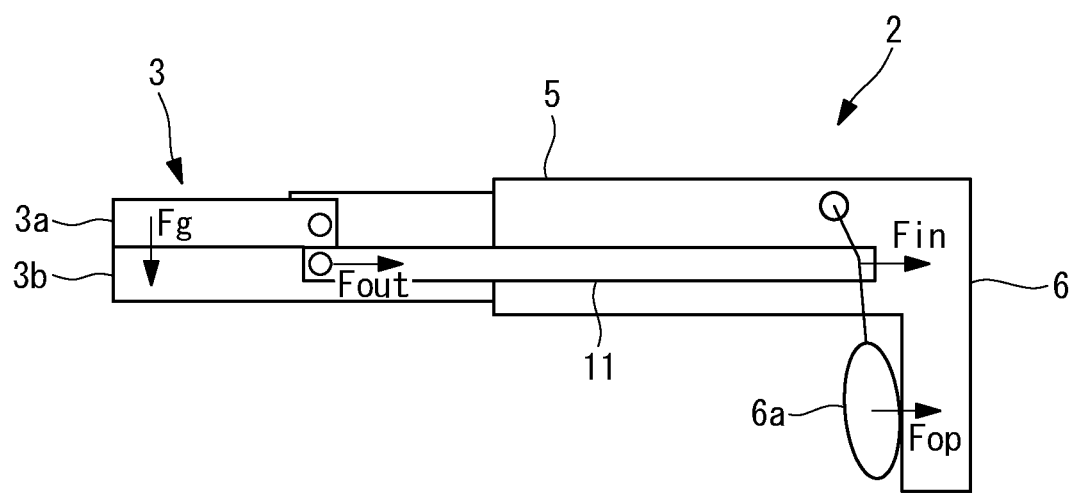
FIG. 18C is a schematic diagram of a modification of the treatment tool in FIG. 1 and shows the gripped state of the end effector.

In this embodiment, the closing operation and the gripping operation of the end effector 3 are performed by means of the pushing force; however, alternatively, as shown in FIGS. 18A to 18C, a configuration in which these operations are performed by means of a pulling force (motive power) Fin may be employed. In this case, the operating portion 6 generates the pushing force when the handle 6a is operated in the opening direction C and generates the pulling force when the handle 6a is operated in the closing direction D.

Figure 19A:
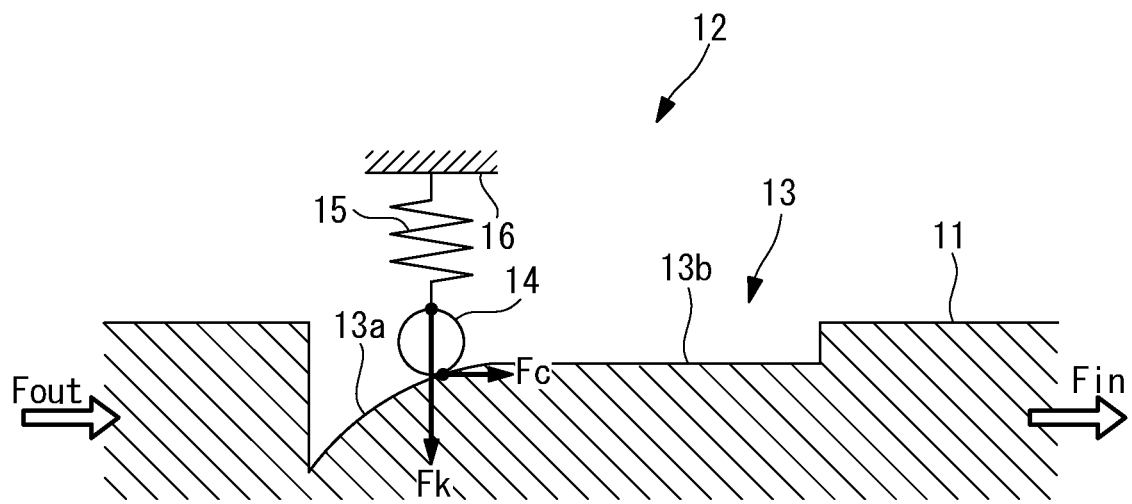
FIG. 19A is a configuration diagram of the adjusting mechanism included in the motive-power transmitting mechanism of the treatment tool in FIG. 18A and shows the positional relationship between the inclined surface and the movable member when the end effector is in the gripped state and the joint portion is not flexed.
Figure 19B:
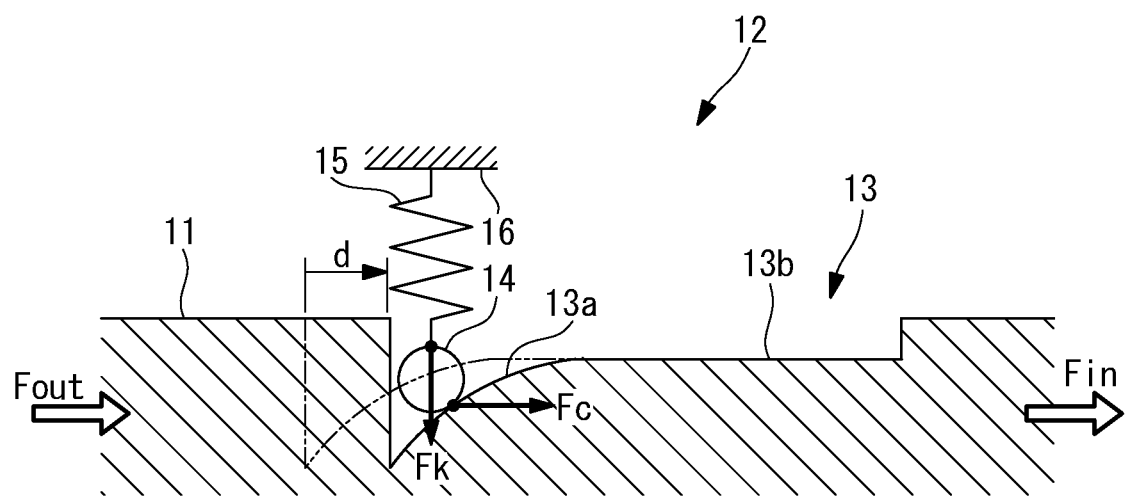
FIG. 19B is a configuration diagram of the adjusting mechanism included in the motive-power transmitting mechanism of the treatment tool in FIG. 18A and shows the positional relationship between the inclined surface and the movable member when the end effector is in the gripped state and the joint portion is flexed.

In the modification in FIGS. 18A to 18C, because the direction of a pulling force Fin is the same as the direction of the displacement of the driving member 11 due to flexing of the joint portion 4, the elastic force Fk of the compression spring 15 decreases with an increase in the displacement amount d as shown in FIGS. 19A and 19B. Therefore, in order to increase the component force Fc in the same direction as the direction of the pulling force Fin (in other words, to increase the magnitude of the component force Fc)

with an increase in the displacement amount d, the inclined surface 13a is a curved surface in which the inclination angle θ continuously and monotonically changes, and satisfies the following Expression (2):

$$Fk1 \times \tan θ1 < Fk2 \times \tan θ2 \qquad (2).$$

Figure 20A:
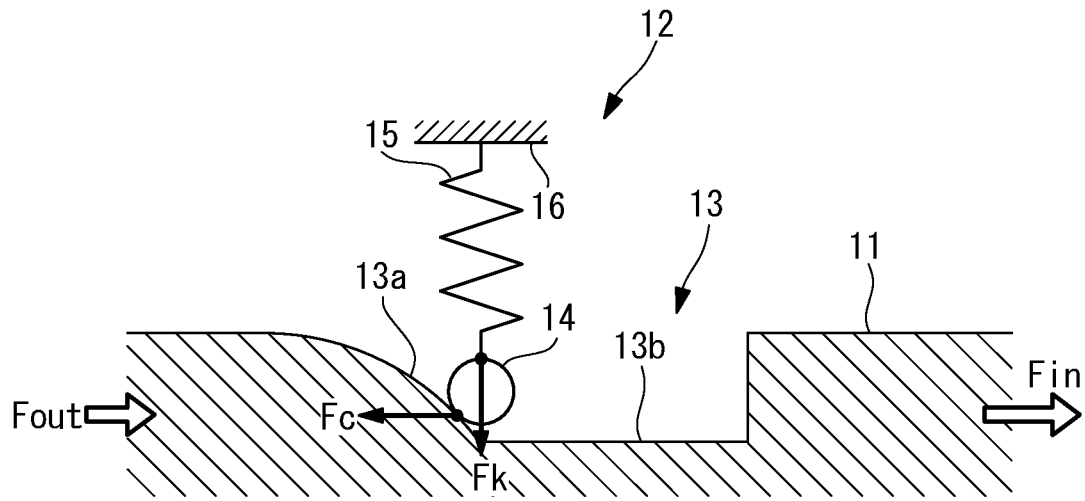
FIG. 20A is a diagram showing a modification of the inclined surface in the adjusting mechanism in FIG. 19A and shows the positional relationship between the inclined surface and the movable member when the end effector is in the gripped state and the joint portion is not flexed.
Figure 20B:
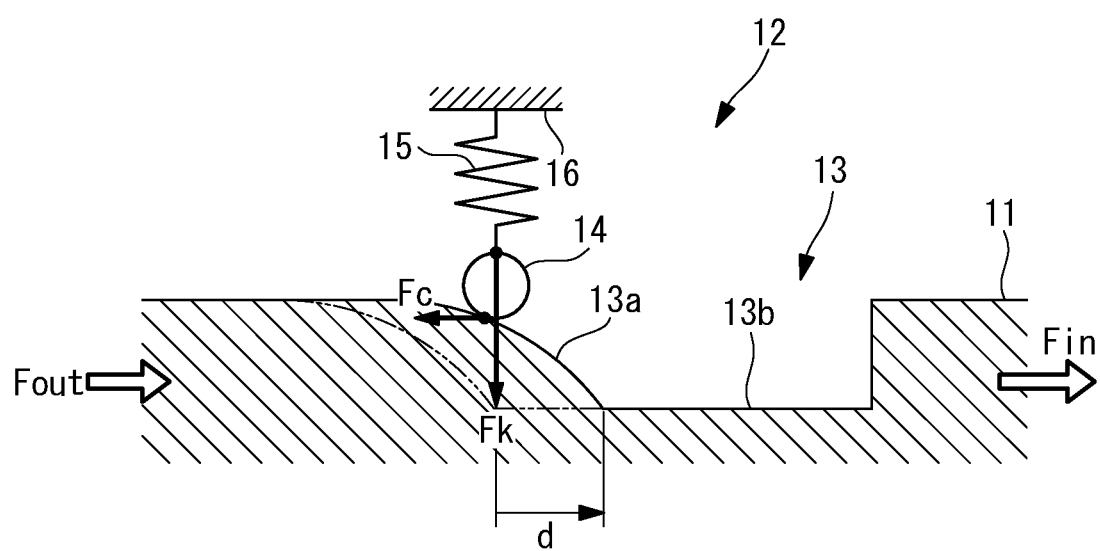
FIG. 20B is a diagram showing a modification of the inclined surface in the adjusting mechanism in FIG. 19A and shows the positional relationship between the inclined surface and the movable member when the end effector is in the gripped state and the joint portion is flexed.

In the modification in FIGS. 18A to 18C, the inclined surface 13a may be formed so as to generate the component force Fc in the opposite direction from the direction of the pulling force Fin, as shown in FIGS. 20A and 20B. In this case, the compression amount and the elastic force Fk of the compression spring 15 increase with an increase in the displacement amount d. Therefore, in order to increase the component force Fc in the same direction as the direction of the pulling force Fin (in other words, to decrease the magnitude of the component force Fc) with an increase in the displacement amount d, the inclined surface 13a is a curved surface in which the inclination angle θ continuously and monotonically changes, and satisfies the following Expression (1):

$$Fk1 \times \tan θ1 > Fk2 \times \tan θ2 \qquad (1).$$

Although this embodiment includes the joint portion 4 having one flexion axis B, the specific form of the joint portion 4 is not limited thereto, and a joint portion in another form that can be flexed or bent in a direction intersecting the longitudinal axis of the insertion portion 5 may be employed.

For example, the joint portion may be a bending portion that has a plurality of flexion axes, which are arranged in the direction along the longitudinal axis A so as to be parallel to each other, and that can be bent at a relatively large radius of curvature, or the joint portion may be a bending portion that can be bent due to flexibility thereof.

In addition, the joint portion may be an insertion portion 5 possessing flexibility, and the adjusting mechanism 12 may be configured so as to generate a component force in accordance with the bending angle of the insertion portion 5 in the body. When the insertion portion 5 is deformed into a bent shape from a straight shape, the pathway length of the driving member 11 such as a wire that passes through inside the insertion portion 5 changes, and thus, the driving member 11 is displaced in the longitudinal direction. Therefore, for example, as a result of providing the adjusting mechanism 12 in the proximal-end portion, which is a portion of the insertion portion 5 and is disposed outside the body, it is possible to compensate for, in accordance with the displacement of the driving member 11, the deterioration of the motive-power transmission efficiency of the driving member 11 associated with bending of the insertion portion 5 by means of the component force generated by the adjusting mechanism 12.

This embodiment includes the operating portion 6 that generates a motive power by means of the manual operation by an operator; however, alternatively, a driving portion that generates a motive power by means of an electric motor may be employed as a motive-power generating portion. For example, an operator inputs an operating signal for moving the end effector 3 to an operation input device (not shown) that is separate from the treatment tool 2. The operating signal is transmitted to the driving portion from the operation input device, an electric motor generates a motive power corresponding to the operating signal, and the motive power is input to the driving member 11 from the electric motor.

As a result, the above-described embodiment leads to the following aspects.

An aspect of the present invention is directed to a motive-power transmitting mechanism that is provided in a treatment tool including an end effector, a joint portion that can be flexed or bent, and a motive-power generating portion that generates a motive power, which are disposed in order from a distal-end side, and that transmits the motive power to the end effector from the motive-power generating portion, the motive-power transmitting mechanism including: an elongated driving member that passes through the joint portion, that connects the end effector and the motive-power generating portion, and that transmits the motive power to the end effector; a force receiving portion that is provided in one of the driving member and a stationary member disposed in an area surrounding the driving member and that has an inclined surface inclined with respect to a longitudinal axis of the driving member; a movable member that is supported with respect to the other one of the driving member and the stationary member so as to be movable in an orthogonal direction with respect to the longitudinal axis and that can be slid along the inclined surface; and a biasing member that biases the movable member in the orthogonal direction toward the inclined surface, wherein the inclined surface generates a component force in a direction parallel to the longitudinal axis on the basis of a biasing force of the biasing member received from the movable member, and the component force increases in the same direction as the direction of the motive power with an increase in the displacement amount of the driving member in a direction along the longitudinal axis in association with flexing or bending of the joint portion.

With this aspect, as a result of the motive power generated by the motive-power generating portion being transmitted to the end effector by the driving member, the end effector performs a mechanical operation. As a result of the driving member, which bridges across the joint portion, also being flexed or bent when the joint portion is flexed or bent, the driving member is displaced with respect to the stationary member in a direction along the longitudinal axis, and the motive-power transmission efficiency thereof also deteriorates.

Meanwhile, due to the biasing force of the biasing member that acts on the inclined surface of the force receiving portion from the movable member, the component force having a magnitude in accordance with the magnitude of the biasing force and the inclination angle of the inclined surface acts on the driving member. The component force generated by the inclined surface increases in the same direction as the direction of the motive power with an increase in the displacement amount of the driving member. Therefore, it is possible to satisfactorily compensate for the deterioration of the motive-power transmission efficiency of the driving member by means of an increase in the component force. Accordingly, it is possible to transmit the motive power to the end effector at a substantially constant efficiency regardless of flexing or bending of the joint portion.

In the above-described aspect, the direction of the component force may be opposite from the direction of the motive power, and Expression (1) below may be satisfied:

$$Fk1 \times \tan θ1 > Fk2 \times \tan θ2 \qquad (1),$$

where Fk1 is the magnitude of the biasing force generated by the biasing member when the joint portion is not flexed or bent, θ1 is the inclination angle of the inclined surface at a contact point with the movable member when the joint portion is not flexed or bent, Fk2 is the magnitude of the biasing force generated by the biasing member when the joint portion is flexed or bent, and θ2 is the inclination angle of the inclined surface at the contact point with the movable member when the joint portion is flexed or bent.

When the direction of the component force is opposite from the direction of the motive power, it is necessary to decrease the magnitude of the component force by flexing or bending the joint portion in order to compensate for the deterioration of the motive-power transmission efficiency of the driving member due to flexing or bending of the joint portion. As a result of the magnitude of the biasing force and the inclination angle satisfying Expression (1), it is possible to decrease the magnitude of the component force in the state in which the joint portion is flexed or bent as compared with the magnitude of the component force in the state in which the joint portion is not flexed or bent.

In the above-described aspect, the direction of the component force may be the same as the direction of the motive power, and Expression (2) below may be satisfied:

$$Fk1 \times \tan \theta 1 < Fk2 \times \tan \theta 2 \qquad (2),$$

where Fk1 is the magnitude of the biasing force generated by the biasing member when the joint portion is not flexed or bent, θ1 is the inclination angle of the inclined surface at a contact point with the movable member when the joint portion is not flexed or bent, Fk2 is the magnitude of the biasing force generated by the biasing member when the joint portion is flexed or bent, and θ2 is the inclination angle of the inclined surface at the contact point with the movable member when the joint portion is flexed or bent.

When the direction of the component force is the same as the direction of the motive power, it is necessary to increase the magnitude of the component force by flexing or bending the joint portion in order to compensate for the deterioration of the motive-power transmission efficiency of the driving member due to flexing or bending of the joint portion. As a result of the magnitude of the biasing force and the inclination angle satisfying Expression (2), it is possible to increase the magnitude of the component force in the state in which the joint portion is flexed or bent as compared with the magnitude of the component force in the state in which the joint portion is not flexed or bent.

The above-described aspect may include a releasing mechanism that releases biasing of the movable member by the biasing member.

When the direction of the component force is the same as the direction of the motive power, the component force in the same direction as the direction of the motive power acts on the driving member also in a state in which the motive power is not input to the driving member from the motive-power generating portion. As a result of releasing, by means of the releasing mechanism, biasing of the movable member by the biasing member, it is possible to release the component force that acts on the driving member.

In the above-described aspect, the biasing member may be provided in the other one of the driving member and the stationary member and supports the movable member so as to be movable in the orthogonal direction, and the magnitude of the biasing force may change in accordance with the displacement amount of the movable member in the orthogonal direction.

Because the displacement amount of the movable member in the orthogonal direction changes in accordance with the displacement amount of the driving member in the direction along the longitudinal axis, the magnitude of the biasing force changes in accordance with the displacement amount of the driving member. Therefore, it is possible to satisfactorily compensate for the deterioration of the motive-power transmission efficiency of the driving member by means of an increase in the component force by changing the magnitude of the component force generated by the inclined surface in accordance with the displacement amount of the driving member.

In the above-described aspect, the biasing member may include a spring that elastically deforms due to the displacement of the movable member in the orthogonal direction.

With this configuration, it is possible to generate, by employing a simple structure, a biasing force that changes in accordance with the displacement amount of the driving member.

In the above-described aspect, the inclination angle of the inclined surface with respect to the longitudinal axis may change in the direction along the longitudinal axis.

The conversion efficiency to the component force from the biasing force is determined by the inclination angle of the inclined surface, and the magnitude of the component force increases with an increase in the inclination angle. Therefore, it is possible to change the magnitude of the component force by means of changes in the inclination angle.

In the above-described aspect, the inclination angle may continuously and monotonically change in the direction along the longitudinal axis.

With this configuration, it is possible to generate, by means of the inclined surface, the component force that gradually increases or decreases in the same direction in accordance with the displacement amount of the driving member.

Another aspect of the present invention is directed to a treatment tool including: an end effector, a joint portion that can be flexed or bent, and a motive-power generating portion that generates a motive power, which are disposed in order from a distal-end side; and any one of the above-described motive-power transmitting mechanisms that transmit the motive power to the end effector from the motive-power generating portion.

The present invention affords an advantage in that it is possible to transmit a motive power to an end effector at a constant efficiency regardless of flexing or bending of a joint portion.

REFERENCE SIGNS LIST 1 motive-power transmitting mechanism
2 treatment tool
3 end effector
4 joint portion
5 insertion portion
6 operating portion (motive-power generating portion)
6a handle
11 driving member
12 adjusting mechanism
13 force receiving portion, slit
13a inclined surface
14 movable member
15 compression spring (biasing member)
151, 152, 154, 155 magnet (biasing member)
153 tension spring (biasing member)
156 constant load spring (biasing member)
16 stationary member
Fc component force
Fin pushing force, pulling force (motive power)
Fout pushing force, pulling force (motive power)
Fg gripping force
Fop operating force

The invention claimed is:

1. A motive-power transmitting mechanism comprising:
   an elongated body connecting an end effector and an operation portion, the elongated body deformable between a bent state and a straight state, the elongated body configured to transmit a motive power generated by the operation portion to the end effector; and
   a biasing body disposed between the elongated body and a stationary body, the biasing body configured to bias the elongated body in a direction intersecting a longitudinal axis direction of the elongated body,
   wherein an output force of the elongated body at the bent state is larger than the output force at the straight state in the longitudinal axis direction of the elongated body.

2. The motive-power transmitting mechanism according to claim 1, further comprising:
   a force receiving portion provided in one of the elongated body and the stationary body, the force receiving portion having an inclined surface inclined relative to a longitudinal axis of the elongated body; and
   a movable body configured to move along the inclined surface, the movable body configured to be biased toward the inclined surface by the biasing body, and
   the inclined surface generates a component force in a direction parallel to the longitudinal axis of the elongated body on a basis of the biasing force received from the movable body.

3. The motive-power transmitting mechanism according to claim 2,
   wherein the direction of the component force is opposite from a direction of the motive power, and
   Expression (1) below is satisfied:

$$Fk1 \times \tan\theta1 > Fk2 \times \tan\theta2 \quad (1),$$

where Fk1 is a magnitude of the biasing force generated by the biasing body when the elongated body is not bent,
   θ1 is an inclination angle of the inclined surface at a first contact point with the movable body when the elongated body is not bent,
   Fk2 is a magnitude of the biasing force generated by the biasing body when the elongated body is bent, and
   θ2 is an inclination angle of the inclined surface at a second contact point with the movable body when the elongated body is bent.

4. The motive-power transmitting mechanism according to claim 2,
   wherein the direction of the component force is the same as a direction of the motive power, and
   Expression (2) below is satisfied:

$$Fk1 \times \tan\theta1 < Fk2 \times \tan\theta2 \quad (2),$$

where Fk1 is a magnitude of the biasing force generated by the biasing body when the elongated body is not bent,
   θ1 is an inclination angle of the inclined surface at a first contact point with the movable body when the elongated body is not bent,
   Fk2 is a magnitude of the biasing force generated by the biasing body when the elongated body is bent, and
   θ2 is an inclination angle of the inclined surface at a second contact point with the movable body when the elongated body is bent.

5. The motive-power transmitting mechanism according to claim 4, further comprising a releasing mechanism configured to release biasing by the biasing body.

6. The motive-power transmitting mechanism according to claim 2,
   wherein the biasing body is provided in an other of the elongated body and the stationary body and supports the movable body so as to be movable in an orthogonal direction relative to the longitudinal axis, and
   a magnitude of the biasing force changes in accordance with the displacement amount of the movable body in the orthogonal direction.

7. The motive-power transmitting mechanism according to claim 6, wherein the biasing body comprises a spring configured to elastically deform due to the displacement of the movable body in the orthogonal direction.

8. The motive-power transmitting mechanism according to claim 2, wherein an inclination angle of the inclined surface relative to the longitudinal axis changes in a longitudinal axis direction.

9. The motive-power transmitting mechanism according to claim 8, wherein the inclination angle continuously and monotonically changes in the longitudinal axis direction.

10. The motive-power transmitting mechanism according to claim 2, wherein the movable body is configured to slide along the inclined surface.

11. The motive-power transmitting mechanism according to claim 1, wherein the elongated body is movable within a range of motion in the bent state, in a first portion of the range of motion the output force varies, and in a second portion of the range of motion the output force is constant.

12. A treatment tool comprising:
    an end effector;
    an elongated body connecting the end effector and an operation portion, the elongated body deformable between a bent state and a straight state, the elongated body configured to transmit a motive power generated by the operation portion to the end effector; and
    a biasing body disposed between the elongated body and a stationary body, the biasing body configured to bias the elongated body in a direction intersecting a longitudinal axis direction of the elongated body,
    wherein an output force of the elongated body at the bent state is larger than the output force at the straight state the longitudinal axis direction of the elongated body.

13. The treatment tool according to claim 12, further comprising:
    a force receiving portion provided in one of the elongated body and the stationary body, the force receiving portion having an inclined surface inclined relative to the longitudinal axis of the elongated body; and
    a movable body configured to move along the inclined surface, the movable body configured to be biased toward the inclined surface by the biasing body, and
    the inclined surface generates a component force in a direction parallel to the longitudinal axis direction of the elongated body on a basis of the biasing force received from the movable body.

14. The treatment tool according to claim 13,
    wherein the direction of the component force is opposite from a direction of the motive power, and
    Expression (1) below is satisfied:

$$Fk1 \times \tan\theta1 > Fk2 \times \tan\theta2 \quad (1),$$

where Fk1 is a magnitude of the biasing force generated by the biasing body when the elongated body is not bent,
    θ1 is an inclination angle of the inclined surface at a first contact point with the movable body when the elongated body is not bent, Fk2 is a magnitude of the biasing force generated by the biasing body when the elongated body is bent, and θ2 is an inclination angle of the inclined surface at a second contact point with the movable body when the elongated body is bent.

15. The treatment tool according to claim 13, wherein the biasing body is provided in an other of the elongated body and the stationary body and supports the movable body so as to be movable in an orthogonal direction relative to the longitudinal axis, and a magnitude of the biasing force changes in accordance with the displacement amount of the movable body in the orthogonal direction.

16. The treatment tool according to claim 15, wherein the biasing body comprises a spring configured to elastically deform due to the displacement of the movable body in the orthogonal direction.

17. The treatment tool according to claim 13, wherein an inclination angle of the inclined surface relative to the longitudinal axis changes in a longitudinal axis direction.

18. The treatment tool according to claim 13, wherein the direction of the component force is the same as the direction of the motive power, and Expression (2) below is satisfied:

$$Fk1 \times \tan \theta 1 < Fk2 \times \tan \theta 2 \qquad (2),$$

where Fk1 is a magnitude of the biasing force generated by the biasing body when the elongated body is not bent, θ1 is an inclination angle of the inclined surface at a first contact point with the movable body when the elongated body is not bent, Fk2 is a magnitude of the biasing force generated by the biasing body when the elongated body is bent, and θ2 is an inclination angle of the inclined surface at a second contact point with the movable body when the elongated body is flexed or bent.

19. The treatment tool according to claim 18, further comprising a releasing mechanism configured to release biasing by the biasing body.

20. The treatment tool according to claim 12, wherein the elongated body is movable within a range of motion in the bent state, in a first portion of the range of motion the output force varies, and in a second portion of the range of motion the output force is constant.

\* \* \* \* \*